US006365359B1

(12) United States Patent
Prusiner et al.

(10) Patent No.: US 6,365,359 B1
(45) Date of Patent: Apr. 2, 2002

(54) INHIBITORS OF PRION FORMATION

(75) Inventors: Stanley B. Prusiner; Fred E. Cohen, both of San Francisco; Thomas L. James, Nicasio, all of CA (US); Kiyotoshi Kaneko, Kodaira (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/439,921

(22) Filed: Nov. 12, 1999

Related U.S. Application Data

(63) Continuation-in-part of application No. 08/868,162, filed on Jun. 2, 1997, now Pat. No. 5,962,669, and a continuation-in-part of application No. 09/076,606, filed on May 12, 1998.

(51) Int. Cl.[7] .......................... G01N 33/53; C07K 14/00
(52) U.S. Cl. .............................. 435/7.1; 574/2; 530/350
(58) Field of Search ......................... 530/350; 435/69.1, 435/252.3, 320.1; 574/2

(56) References Cited

U.S. PATENT DOCUMENTS

| | | |
|---|---|---|
| 5,025,388 A | 6/1991 | Cramer, III et al. |
| 5,307,287 A | 4/1994 | Cramer, III et al. |
| 5,434,796 A | 7/1995 | Weininger |
| 5,526,281 A | 6/1996 | Chapman et al. |

FOREIGN PATENT DOCUMENTS

| | | |
|---|---|---|
| WO | WO 91/19810 | 12/1991 |
| WO | WO 93/10227 | 5/1995 |

OTHER PUBLICATIONS

Demaimay et al. 1997. J. Virology 71(12): 9685–9689.*
Kaneko et al. 1995. PNAS 92: 11160–11164.*
Baker, H.F., et al. "Aminoacid Polymorphism in Human Prion Protein and Age at Death in Inherited Prion Disease," *Lancet* (1991) 337:1286.
Barry, R.A., et al., "Monoclonal Antibodies to the Cellular and Scrapie Prion Proteins," *J. Infect. Dis.* (1986) 154(3):518–521.
Basler et al., "Scrapie and Cellular PrP Isoforms Are Encoded by the Same Chromosomal Gene,"0 *Cell,* (1986) 46:417–28.
Berger, J.R., et al., "Creutzfeldt–Jakob disease in a physician: A review of the disorder in health care workers", *Neurology,* (1993) 43:205–206.
Bolton et al., "Identification of a Protein That Purifies with the Scrapie Prion," *Science* (1982) 218: 1309–11.
Brown et al., "Friendly Fire' in Medicine: Hormones, Homografts, and Cruetzfeldt–Jakob Disease," *Lancet* (1992) 340: 24–27.

Buchanan et al., "Mortality, Neoplasia, and Creutzfeld–Jakob Disease in Patients Treated with Human Pituitary Growth Hormone in the United Kingdom", *BMJ* (1991) 302:824–828.
Bueler et al., "Mice Devoid of PrP are Resistant to Scrapie," *Cell* (1993) 73:1339–1347.
Bueler et al., "Normal Development and Behavior of Mice Lacking the Neuronal Cell–surface PrP Protein," *Nature* (1992) 356:577–582.
Carlson et al., "Linkage of Protein and Scrapie Incubation Time Genes," *Cell* (1986) 46:503–511.
Chandler, "Encephaolpathy in Mice Produced by Inoculation with Scrapie Brain Material," *Lancet* (1961) 1:1378–79.
Cochius et al, "Creutzfeldt–Jakob Disease in a Recipient of Human Pituitary–Derived Gonadotrophin: A Second Case," *J. Neurol. Neurosurg. Psychiatry* (1992) 55:1094–1095.
Cochius et al., "Creutzfeldt–Jakob Disease in a Recipient of Human Pituitary–Derived Gonadotrophin," *Aust. N.Z. J. Med.* (1990) 20:592–593.
Cohen, F.E., et al., "Structural Clues to Prion Replication," *Science* (Apr. 22, 1994) 264:530–531.
Collinge et al., "Genetic Predisposition to Latrogenic Creutzfeldt–Jakob Disease," *Lancet* (1991) 337:1441–1442.
Cousens, S.N., et al., "Geographical distribution of cases of Creutzfeldt–Jakob disease in England and Wales 1970–84", *J. Neurol. Neurosurg. Psychiatry* (1990) 53:459–465.
Farlie, P.G., et al., "bcl–2 Transgene expression can protect neurons against developmental and induced cell death", *Proc. Natl. Acad. Sci. USA* (1995) 92:4397–4401.
Gabriel et al., "Molecular Cloning of a Candidate Chicken Prion Protein," *Proc. Natl. Acad. Sci. USA* (1992) 89:9097–9101.
Gajdusek, D.C., "Unconventional Viruses and the Origin and Disappearance of Kuru," *Science* (1977) 197:943–960.
Gibbs, Jr. et al., "Creutzfeldt–Jakob Disease Infectivity of Growth Hormone Derived from Human Pituitary Glands," *N.Engl. J. Med.* (1993) 328:358–359.
Goldfarb et al, "Fatal Familial Insomnia and Familial Creutzfeldt–Jakob Disease: Disease Phenotype Determined by a DNA Polymorphism," *Science* (1992) 258:806–808.
Goldmann et al., "Two Alleles of a Neural Protein Gene Linked to Scrapie in Sheep," *Proc. Natl. Acad. Sci. USA* (1990) 87:2476–2480.

(List continued on next page.)

Primary Examiner—Karen Cochrane Carlson
(74) Attorney, Agent, or Firm—Karl Bozicevic; Bozicevic, Field & Francis LLP

(57) ABSTRACT

Molecules are disclosed that interact with the cellular components involved in conversion of $PrP^C$ to $PrP^{Sc}$. The molecules disclosed can be small molecules, peptides or protein analogs, e.g. analogs of $PrP^C$. In one embodiment, these molecules interfere with prion formation and/or replication, e.g. by preventing interactions of proteins involved in a prion complex or by interfering with β-sheet formation. In another embodiment, the molecules of the invention promote $PrP^C$ conversion to $PrP^{Sc}$, e.g. by binding to $PrP^C$ and facilitating a conformational change from $PrP^C$ to $PrP^{Sc}$.

1 Claim, 5 Drawing Sheets

OTHER PUBLICATIONS

Figure 1:
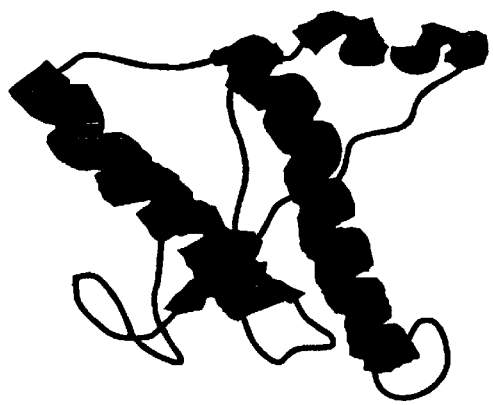

Goldmann et al., "Different Forms of the Bovine PrP Gene Have Five or Six Copies of a Short, G–C Rich Element within the protein–coding Exon," *J. Gen. Virol.* (1991) 72:201–204.

Harris et al., "A Prion–like Protein from Chicken Brain Copurifies with an Acetylcholine Receptor–Inducing Activity," *Proc. Natl. Acad. Sci. USA* (1991) 88:7664–7668.

Hasty, P., et al., "Introduction of a subtle mutation into the Hox–2.6 locus in embryonic stem cells", *Nature* (1991) 350:243–246.

Healy et al., "Creutzfeldt–Jakob Disease After Pituitary Gonadotrophins: The Prion is the Problem," *BMJ* (1993) 307:517–518.

Hecker et al., "Replication of Distinct Scrapie Prion Isolates is Region Specific in Brains of Transgenic Mice and Hamsters," *Genes Dev.* (1992) 6:1213–1228.

Hsaio et al.,"Linkage of a Prion Protein Missense Variant to Gerstmann–Straussler Syndrome," *Nature* (1989) 383:342–345.

Hsaio et al., "A Prion Protein Variant in a Family with the Telencephalic Form of Gerstmann–Strussler–Scheinker Syndrome," *Neurology* (1991) 41:681–684.

Hsaio et al., "Inherited Human Prion Diseases," *Neurology* (1990) 40:1820–1827.

Kaneko, K. et al., "Evidence for protein X binding to a discontinuous epitope on the cellular prion protein during scrapie prion propagation," *Proc Natl Acad Sci USA* (Sep. 1977) 94:10069–10074.

Kascsak, R.J., et al., "Mouse Polyclonal and Monoclonal Antibody to Scrapie–Associated Fibril Proteins," *J. Virol.* (1987) 61(12):3688–3693.

Koch et al.,"Creutzfeldt–Jakob Disease in a Young Adult with Idiopathic Hypopituitarism," *N. Engl. J. Med.* (1985) 313:731–733.

Kretzschmar et al., "Molecular Cloning of a Human Prion Protein cDNA," *DNA* (1986) 5:315–324.

Kretzschmar et al., "Molecular Cloning of a Mink Prion Protein Gene," *J.Gen.Virol.* (1992) 73:2757–2761.

Lasmezas et al.,"Recombinant Human Growth Hormone and Insulin–Like Growth Factor I Induce PRP Gene Expression in PC12 Cell," *Biochem. Biophys. Res.Commun.* (1993) 196:1163–1169.

Locht et al.,"Molecular Cloning and Complete Sequence of Prion Protein cDNA from Mouse Brain Infected with the Scrapie Agent," *Proc. Natl. Acad. Sci USA* (1986) 83:6372–6376.

Manuelidis et al., "Serial Propagation of Creutzfeldt–Jakob Disease in Guinea Pigs," *Proc. Natl. Acad. Sci. USA* (1976) 73:223–227.

Manuelidis et al., "Interspecies Transmission of Creutzfeldt–Jakob Disease to Syrian Hamsters with Reference to Clinical Syndromes and Strain of Agent," *Proc. Natl. Acad. Sci USA* (1978) 75:3432–3436.

McKinley et al, "A Protease–Resistant Protein is a Structural Component of the Scrapie Prion," *Cell* (1983) 35:57–62.

Medori et al., "Fatal Familial Insomnia, a Prion Disease with a Mutation at Codon 178 of the Prion Protein Gene," *N. Engl.J. Med.* (1992) 326:444–449.

Muramoto, T., et al., "The Sequential Development of Abnormal Prion Protein Accumulation in Mice with Creuzfeldt–Jakob Disease," *Am. J. Pathol.* (1992) 140(6):1411–1420.

Nisbet et al., "Creutzfeldt–Jakob Disease in a Second Patient Who Received a Cadaveric Dura mater Graft," *J.Am. Med.Assoc.* (1989) 261:1118.

Palmer, M.S., et al., "Homozygous Prion Protein Genotype Predisposes to Sporadic Creutzfeldt–Jakob Disease", *Nature* (1991) 352:340–342.

Patel, "France Reels at Latest Medical Scandal," *New Scientist,* Jul. 31, 1993, p. 4.

Patel, "Placenta Donors to be Screened for Brain Disease," *New Scientist,* Nov. 20, 1993, p. 10.

Pan, K.M., et al., "Conversion of β–sheets features in the formation of the scrapie prion proteins", *Proc. Natl. Acad. Sci. USA* (1993) 90:10962–10966.

Prusiner et al., "Measurement of the Scrapie Agent Using an Incubation Time Interval Assay," *Annals. Neurol.* (1982) 11(4):353–358.

Prusiner et al., "Further Purification and Characterization of Scrapie Prions," *Biochemistry* (1982) 21:6942–50.

Prusiner, S.B., et al., "Scrapie Prions Aggregate to Form Amyloid–like Birefringent Rods," *Cell* (1983) 35:349–358.

Prusiner et al., "Transgenic Studies Implicate Interactions Between Homologous PrP Isoforms in Scrapie Prion Replication," *Cell* (1990) 63:673–686.

Prusiner et al., "Molecular Biology of Prion Diseases," *Science* (1991) 252:1515–1522.

Prusiner et al., "Ablation of the Prion Protein (PrP) Gene in Mice Prevents Scrapie and Facilitates Production of AntiPrP Antibodies," *Proc. Natl. Acad. Sci. USA* (1993) 90:10608–10612.

Prusiner, S.B., et al., "Immunologic and Molecular Biological Studies of Prion Proteins in Bovine Spongiform Encephalopathy," *J. Infect. Dis.* (1993) 167:602–613.

Prusiner et al., "Prion Diseases and Neurodegeneration," *Ann.Rev.Neurosci.* (1994) 17:311–339.

Prusiner, S.B., et al., "Prion Protein Biology," *Cell* (May 1, 1998) 93:337–348.

Raeber et al., "Attempts to Convert the Cellular Prion Protein into the Scrapie Isoform in Cell–Free Systems," *J. Virol.* (1992) 66:6155–6163.

Ridley et al., *Lancet* Occupational Risk of Creuzfeldt–Jakob Disease, (1993) 341:641–2.

Rogers, M. et al., "Epitope Mapping of the Syrian Hamster Prion Protein Utilizing Chimeric and Mutant Genes in a Vaccinia Virus Expression System," *J. Immunol.* (1991) 147(10):3568–3574.

Scott, M., et al, "Transgenic Mice Expressing Hamster Prion Protein Produce Species–Specific Infectivity and Amyloid Plaques," *Cell* (1989) 59:847–857.

Scott et al, "Chimeric Prion Protein Expression in Cultured Cells and Transgenic Mice," *Protein Sci.* (1992) 1:986–97.

Scott et al, "Propagation of Prions with Artificial Properties in Transgenic Mice Expressing Chimeric PrP Genes," *Cell* (1993) 73:979–988.

Serban, D., et al. "Rapid detection of Creutzfeldt–Jakob disease and scrapie prion proteins", *Neurology* (1990) 40:110–117.

Stahl et al., "Glycosylinositol Phospholipid Anchors of the Scrapie and Cellular Prion Proteins Contain Sialic Acid," *Biochemistry* (1992) 31:5043–5053.

Taraboulos et al., "Regional Mapping of Prion Proteins in Brain," *Proc. Natl. Acad. Sci. USA* (1992) 89:7620–7624.

Tateishi, J. and Kitamoto, T., "Developments in Diagnosis for Prion Diseases," *Br. Med. Bull.* (1993) 49(4):971–979.

Tateishi et al.,"Transmission of Chronic Spongiform Encephalopathy with Kuru Plaques from Humans to Small Rodents," *Ann.Neurol.* (1979) 5:581–584.

Telling, G.C. et al., "Prion Propagation in Mice Expressing Human and Chimeric PrP Transgenes Implicates the Interaction of Cellular PrP with Another Protein," *Cell* (Oct. 6, 1995) 83:79–90.

Telling, G.C., et al., "Transmission of Creutzfeldt–Jakob disease from humans to transgenic mice expressing chimeric human–mouse prion protein," *Proc Natl Acad Sci USA* (Oct. 1994) 91:9936–9940.

Thadani et al., "Creutzfeldt–Jakob Disease Probably Acquired From a Cadaveric Dura Mater Graft," *J. Neurosurg.* (1988) 69:766–769.

Valancius, V. and Smithies, O., "Testing and "In–Out" Targeting Procedure for Making Subtle Genomic Modifications in Mouse Embryonic Stem Cells", *Mol. Cell Biol.* (1991) 11(3):1402–1408.

Westaway et al., Homozygosity for Prion Protein Alleles Encoding Glutamine–171 Renders Sheep Susceptible to Natural Scrapie,: *Genes Dev.* (1994) 8:959–969.

Westaway et al., "Degeneration of Skeletal Muscle, Peripheral Nerves, and the Central Nervous System in Transgenic Mice Overexpressing Wild–Type Prion Proteins," *Cell* (1994) 76:117–129.

Willison et al., "Creutzfeldt–Jakob Disease Following Cadaveric Dura Mater Graft," *Neurosurg. Psychiatric* (1991) 54:940.

Wilesmith, J.W., "The epidemiology of bovine spongiform encephalopathy", *Acad. Press.* (1991) 2:239–245.

Yehiely, F., et al., "Identification of candidate proteins binding to prion proteins," *Neurobiology of Disease* (1977) 3(4):339–355.

\* cited by examiner

1. MFCD00114003

2. MFCD00122889

3. MFCD00122890

4. MFCD00219633

5. MFCD00219631

6. MFCD00219634

7. MFCD00663052

8. MFCD00218676

9. MFCD00218674

INHIBITORS OF PRION FORMATION

CROSS-REFERENCE

This application is a continuation-in-part application of Ser. No. 08/868,162, filed Jun. 2, 1997 now U.S. Pat. No. 5,962,669, and Ser. No. 09/076,606, filed May 12, 1998, each of which is incorporated herein by reference in their entirety and to which applications we claim priority under 35 USC §120.

GOVERNMENT RIGHTS

The United States Government may have certain rights in this application pursuant to Grant Nos. NS14069, AG08967, AG02132, NS22786 and AG10770 awarded by the National Institutes of Health.

FIELD OF THE INVENTION

This invention relates generally to proteins, functionally equivalent pharmacophores and methods of creating and/or detecting inhibitors of prion formation. Specifically, the invention relates to small molecules, peptides and peptide analogs with the ability to either inhibit prion formation or replication and methods of treating a neuropathology such as a prion-mediated neuropathology.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not efficiently infect another (e.g., a mouse).

From a clinical perspective, the prion diseases represent a variety of neurodegenerative states characterized at the neuropathologic level by the presence of spongiform degeneration and astrocytic gliosis in the central nervous system (DeArmond & Prusiner (1996) *Current Topics in MicroBiology and Immunology*, 207:125–146). Frequently, protein aggregates and amyloid plaques are seen that are often resistant to proteolytic degradation. The neuroanatomic distribution of the lesions varies with the specific types of prion disease. In humans, sporadic Creutzfeldt-Jakob Disease (CJD) accounts for 85% of all cases. The disease presents in the sixth decade of life with dementia and ataxia. Familial disease carries a variety of monikers such as Gertsmann-Straussler-Scheinker disease (GSS), familial CJD (fCJD) and Fatal Familial Insomnia (FFI) that relate the precise mutation in the PrP gene to a clinical syndrome (Prusiner & Hsaio (1994) *Annals of Neurology*, 35:385–395; Parchi, et al. (1996) *Annals of Neurology*, 39:767–778; Montagna, et al. (1998) *Brain Pathology*, 8:515–520). Disease typically presents in the fourth decade of life with an autosomal dominant pedigree. While the infectious prion diseases represents less than 1% of all cases, their link to mad cow disease in the U.K. (new variant CJD), growth hormone inoculations in the U.S. and France (iatrogenic CJD), and ritualistic cannibalism in the Fore tribespeople (Kuru) have raised the public awareness of this facet of the disease (Devillemeur, et al. (1996) *Neurology*, 47:690–695; Hill, et al. (1997) *Nature*, 389:448–450; Goodfield (1997) *Nature*, 387:841–841).

Figure 2:

A critical advance in our understanding of prion diseases came with the partial purification of a proteinaceous material that retained the ability to reinfect laboratory rodents (McKinley, et al. (1983) *Cell*, 35:57–62). Micro-sequencing and molecular biologic tools led to the cloning of the prion gene, a normal component of mammalian and avian genomes (Prusiner, et al. (1984) *Cell*, 38:127–134). The gene contains a single open reading frame and codes for a protein that is proteolytically processed and glycosylated to form a macromolecule with 219 amino acids, a disulfide bridge, two N-linked sugars and a glycophosphotidyl inositol anchor that is exported to the cell surface and concentrated in an endocytic compartment known as the caveolar space (Endo, et al. *Biochemistry*, 28:8380–8 1989); Stahl, et al. Biochemistry 29:8879–84 (1990); Yost, et al. *Nature*, 343:669–72 (1990); DeFea, et al. *J. Biol. Chem.*, 269:16810–16820 (1994); Hegde, et al., *Science* 279:827–34 (1998)). Biophysical characterization of the deglycosylated recombinant PrP refolded into a monomeric form resembling the normal cellular isoform ($PrP^C$) reveals a two domain molecule with an N-terminal region (57–89) that binds 4 $Cu^{++}$ atoms per chain (Viles, et al. (1999) *Proc. Natl. Acad. Sci. USA*, 96:2042–2047) and a C-terminal region (124–231) that contains 3 substantial helices and 2–3 residue β-strands joined by 2–3 hydrogen bonds (see FIG. 1) (Riek, et al. (1996) *Nature*, 382:180–182; James, et al. (1997) *Proc. Natl. Acad. Sci. USA*, 94:10086–10091; Donne, et al. (1997) *Proc. Natl. Acad. Sci. USA*, 94:13452–13457). By contrast, the disease causing form of the prion protein ($PrP^{Sc}$) is a multimeric assembly substantially enriched in β-sheet structure (40% β-sheet, 30% α-helices as judged by FTIR spectroscopy) (Pan, et al. (1993) *Proc. Natl. Acad. Sci. USA*, 90:10962–10966). Immunologic studies of $PrP^{Sc}$ suggest that the conformational change is largely in the region from residues 90–145 or perhaps 175 (Peretz, et al. (1997) *J. Mol. Biol.* 273:614–622) These features have been codified in a model of $PrP^{Sc}$ (see FIG. 2) that emphasize the dramatic conformational distinction between $PrP^C$ and $PrP^{Sc}$.

Figure 3:
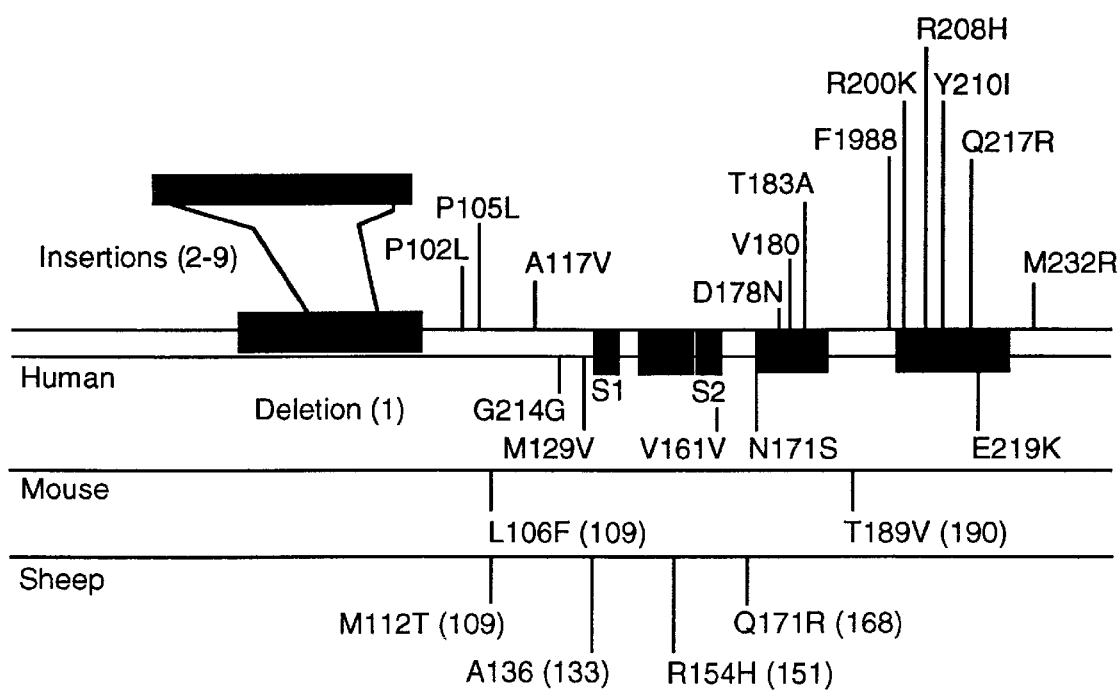

A large number of genetic and transgenetic studies have helped to cement the role of the prion protein in the pathogenesis of this group of neurodegenerative diseases. First, a variety of genetic linkage studies of kindreds with familial prion diseases mapped the defect to the Prn-p locus. Subsequent studies identified specific point mutations that caused inherited disease (Hsiao, et al. (1989) *Nature*, 338:342–345; Dlouhy, et al. (1992) *Nat. Genet.*, 1:64–67; Petersen, et al. (1992) *Neurology*, 42:1859–1863; Poulter, et al. Brain 115:675–85 (1992); Gabizon, et al. (1993) *Am. J. Hum. Genet.*, 53:828–835). These loci are shown in FIG. 3. Subsequently, the Prn-p gene was knocked out in mice with no obvious phenotypic sequelae (Büeler, et al. (1992) *Nature*, 356:577–582). While wild type mice will develop a prion disease ~180d after intracerebral inoculation, the hemizygous animals require ~400d to succumb to an infectious inoculum and the homozygous knockouts are resistant to prion infection (Prusiner, et al. (1993) *Proc. Natl. Acad. Sci. USA*, 90:10608–10612; Büeler, et al. (1994) *Molecular Medicine*, 1:19–30). Transgenic mice carrying a sufficiently high number of copies of mutant gene (the human GSS mutation P101L) on the knockout background develop a spontaneous neurodegenerative disease that is faithful to the neuropathologic expectations developed from a study of the human kindreds. Knockout mice carrying a redacted form of the PrP transgene (90–141; 175–231) also develop a prion disease upon inoculation with full length RML prions (Supattapone, et al. (1999) *Cell*, 96:869–878). The infection process is more efficient with the "mini" RML prion demonstrating that an artificial prion can be created and that replication efficiency demands fidelity at the amino acid sequence level.

While the predominantly helical PrP$^C$ and β-sheet rich PrP$^{Sc}$ have exceptionally different secondary and tertiary structures as judged by CD, FTIR, and NMR spectroscopy (Caughey, et al. (1991) *Biochemistry*, 30:7672–7680; Pan, et al. (1993) *Proc. Natl. Acad. Sci. USA*, 90:10962–10966; Riek, et al. (1996) *Nature*, 382:180–182; James, et al. (1997) *Proc. Natl. Acad. Sci. USA*, 94:10086–10091; Donne, et al. (1997) *Proc. Natl. Acad. Sci. USA*, 94:13452–13457), they appear to share a common amino acid sequence and disulfide bridge (Cohen & Prusiner (1998) *Annual Review of Biochemistry*, 67:793–819). Recent work has shown that a conformational change that is aided by an auxiliary molecule is an obligatory step in PrP$^{Sc}$ formation (Telling, et al. (1995) *Cell*, 83:79–90; Kaneko, et al. (1997) *J. Mol. Biol.* 270:574–586). The exceptional stability of PrP$^{Sc}$ and the marginal stability of PrP$^C$ together with a variety of transgenetic and cellular transfection studies have led to the conclusion that PrP$^C$ is a kinetically trapped intermediate in the folding of PrP$^{Sc}$ (Cohen & Prusiner (1998) *Annual Review of Biochemistry*, 67:793–819). This kinetic barrier can be reduced by exogenous administration of the PrP$^{Sc}$ template, mutations to the wild type (wt) PrP sequence, or stochastic processes resulting in infectious, inherited, or sporadic prion diseases. Epitope mapping and peptide studies suggest that much of this conformational plasticity is localized to the middle third of this 231 residue GPI anchored glycoprotein with a 22 amino acid signal sequence (Peretz, et al. (1997) *J. Mol. Biol.*, 273:614–622).

Peptide fragments derived from regions of the PrP sequence have been studied extensively (Gasset, et al. (1992) *Proc. Natl. Acad. Sci. USA*, 89:10940–10944; Tagliavini, et al. (1993) *Proc. Natl. Acad. Sci. USA*, 90:9678–9682; Forloni, et al. (1993) *Nature*, 362:543–546; Come, et al. (1993) *Proc. Natl. Acad. Sci. USA*, 90:5959–5963; Zhang, et al. (1995) *J. Mol. Biol.*, 250:514–526; Nguyen, et al. (1995) *Biochemistry*, 34:4186–4192; Kaneko, et al. (1997) *J. Mol. Biol.* 270:574–586). In particular, peptides chosen from the region 90–145 are compatible with α-helical, irregularly coiled, and β-sheet rich conformations when characterized under different conditions (Zhang, et al. (1995) *J. Mol. Biol.*, 250:514–526). Furthermore, catalytic amounts of β-sheet rich peptides can facilitate the conformational conversion of peptides with distinct structures into β-sheet rich isoforms (Gasset, et al. (1992) *Proc. Natl. Acad. Sci. USA*, 89:10940–10944; Nguyen, et al. (1995) *Biochemistry*, 34:4186–4192).

More than a million cattle infected with bovine spongiform encephalopathy (BSE) have entered the food chain in the U.K., and fears that BSE has been transmitted to man were raised when new variant (CJD) appeared in the U.K. Since it is hard to predict the number of cases of this disease that may arise in the future, initiation of the search for an effective therapy is essential. No systematic drug discovery efforts have been attempted owing to difficulties in developing a robust screening assay. Many isolated observations with potential therapeutic implications have been made. For example, several compounds are known to inhibit PrP$^{Sc}$ formation in scrapie-infected neuroblastoma cells such as sulfated glycans and the amyloid stain Congo Red (Caughey & Raymond (1991) *J. Biol. Chem.*, 266:18217–18223). However, these compounds are unable to cross the blood-brain barrier, and therefore have no therapeutic benefit after the infection has reached the central nervous system (Caughey, et al. (1993) *J. Virol.*, 67:6270–6272; Ehlers & Diringer (1984) *J. Gen. Virol.*, 651325–1330; Farquhar & Dickinson (1986) *J. Gen. Virol.*, 67:463–473). Other candidates such as polyene antibiotics (Demaimay, et al. (1997) *J. Virol.*, 71:9685–9589) and anthracyclines (Tagliavini, et al. (1997) *Science*, 276:1119–1122) have very low therapeutic indices. Tetrapyrroles inhibit PrP$^{Sc}$ formation and there is some evidence that they can cross the blood-brain barrier (Caughey, et al. (1998) *Proc. Natl. Acad. Sci. USA*, 95:12117–12122), but at this time, the mechanism of action and in vivo efficacy of these compounds is unknown.

There is a need in the art for molecules with the ability to prevent and/or halt the progression of prion-mediated disorders.

SUMMARY OF THE INVENTION

Molecules are disclosed that interact with the cellular components involved in conversion of PrP$^C$ to PrP$^{Sc}$. The molecules disclosed can be small molecules, peptides or protein analogs, e.g. analogs of PrP$^C$. In one embodiment, these molecules interfere with prion formation and/or replication, e.g. by preventing interactions of proteins involved in a prion complex or by interfering with β-sheet formation. In another embodiment, the molecules of the invention promote PrP$^C$ conversion to PrP$^{Sc}$, e.g. by binding to PrP$^C$ and facilitating a conformational change from PrP$^C$ to PrP$^{Sc}$. The molecules may be designed to be species specific, meaning that the molecule will only bind to PrP$^C$ or Prion Protein Modulator Factor (PPMF) of the same or a genetically similar species. Alternatively, the molecules of the invention may be designed to bind to PrP$^C$ or PPMF of genetically a diverse species, i.e. the molecules will not be limited by the "species barrier" that normally limits prion infectivity.

The invention features a pharmacophore (defined here as a compound corresponding to a geometric and chemical description of a molecular structure or collection of molecular structures) characterized by an ability to modulate conversion of PrP$^C$ to PrP$^{Sc}$ in vivo. The pharmacophore can be a peptide or a small molecule with the ability to bind to PPMF and/or PrP$^C$. The structure of the pharmacophore can be defined by a tertiary surface reflecting the negative image of PPMF at its PrP binding domain and/or a tertiary surface defined by the positive image of a specific discontinuous epitope of PrP protein that includes a small subset of residues.

In a preferred embodiment, the pharmacophore structure reflects geometric and chemical positions defined by the relative positions of specific amino acid side chains corresponding to the positions of residues 90–231 of the human PrP protein, and in particular residues 168, 172, 215 and 219 corresponding to the human PrP protein. Optionally or alternatively, the pharmacophore can also contain an epitope from PPMF that binds to PrP.

An object of the invention is to provide an ex vivo system for studying the structural events occurring in conversion, where the system is a cell line treated with a small organic molecule or a peptide that is able to mimic the chemical and geometric features of proteins involved in prion complexing.

An advantage of the present invention is that infectivity of prions in a sample can be determined rapidly.

In another aspect of the invention, the pharmacophore is any one of a collection of molecules that repress prion infectivity and or progression of prion-mediated disease. Any pharmacophore of the invention may inhibit initial infectivity, conversion of PrP$^C$ to PrP$^{Sc}$ and/or progression of neurodegeneration by any number of mechanisms, including but not limited to binding a molecule involved in prion complexing, e.g. PrP$^C$ or PPMF or inhibiting β-sheet formation or elongation.

Yet another aspect of the invention features a method of repressing conversion of PrP$^C$ to PrP$^{Sc}$, comprising administering an inhibitor that meets the criteria specified by the pharmacophore model. This may be administered prophylactically to a subject at risk of developing a prion-mediated disorder, e.g. a mammal exposed to infectious prions, or to treat a subject that is exhibiting signs of prion-mediated neurodegeneration.

A feature of the invention is that the inhibitors can be used to treat subjects suffering from prion-mediated disorders.

Yet another aspect of the invention features an assay to identify a PrP pharmacophore, a geometric and chemical specification of a collection of small molecules that could inhibit PrP$^{Sc}$ formation. The assay utilizes the steps of determining functional residues of the PrP protein involved in prion complex interactions, developing three dimensional structures based on these functional residues, comparing the three dimensional structures with a series of compounds having known or calculated tertiary structures, and identifying compounds having a spatial orientation consistent with binding to components of the PrP$^{Sc}$ replication complex (PrP$^C$, PrP$^{Sc}$, PPMF) at these functional residues.

These and other objects, advantages, and features of the invention will become apparent to those persons skilled in the art upon reading the details of the molecules as more fully described below.

BRIEF DESCRIPTION OF THE DRAWINGS

FIG. 1 is a ribbon drawing of the NMR of rSHa PrP (90–23 1). Residues 90–115 are not shown. α-helical regions are shown in mauve and β-strands are shown in cyan.

FIG. 2 is a model of the putative structure of $PrP^{Sc}$ highlighting the dramatic increase in the β-sheet structure that has been localized to the region between residues 90–145 by immunologic studies.

FIG. 3 illustrates mutations causing inherited human prion disease and polymorphism's in human, mouse and sheep. The x-axis represents the human PrP sequence, with the five octarepeats, the three α-helical A, B and C and the two β-strands S1 and S2. Above the line of the human sequence are mutations that cause prion disease. Below the lines are polymorphisms, some but not all of which are known to influence the onset as well as the phenotpye of disease.

FIG. 4 is an illustration of the distinction between thermodynamic and kinetic models for the energetics of the conversion of $PrP^{C}$ carrying the wild-type (WT) and mutant (MUT) sequences into $PrP^{Sc}$. ΔG is the free energy difference between the $PrP^{C}$ and $PrP^{Sc}$ states and ΔG‡ is the activation energy barrier separation these two states. $\Delta\Delta G^{WT/MUT}$ is the difference between $\Delta G^{WT}$ and $\Delta G^{MUT}$. The free energy diagrams for the wild-type sequences are shown (solid lines), as are the mutant sequences (broken lines).

FIG. 5 is an approach to small molecules in computer screening for inhibitors of $PrP^{Sc}$ replication based on blocking the $PrP^{C}$:PPMF interaction.

FIG. 6 shows dependence of Cp-60 inhibition on $(MHM2)PrP^{Sc}$ concentration using the Time Resolved Fluorescence (TRF) technique of Safar et al (1998). Different concentrations of Cp-60 were applied on transiently transfected ScN2a cells. Samples were digested by proteinase K and the remaining proteins were quantified by immunoassay using the TRF technique. An Eu-mAb3F4 is used to detect (MHM2)PrP proteins. Data represent average+s.e.m. from three independent experiments measured in duplicate.

FIG. 7 illustrates the chemical composition of compound 60.

FIG. 8 illustrates the chemical structure of analogs based on a substructure search using compound 60. FIG. 8 shows the results of a substructure search of the available chemicals directory with compound 60 as a probe. Nine commercially available compounds have been identified and six have been screened.

FIG. 9 is a graphic representation of an open reading frame of the MoPrP and synthetic peptides 89–143 and 89–143, P101L of the MoPrP (MoPrP(89–143)) and MoPrP (89–143, P101L)). The residue corresponding to the mutation is underlined. Confirming that the N-terminal half of the PrP open reading frame is dispensable in prion propagation, PrP27-30 containing G89-S230 can induce prion propagation. HA, HB and HC represent Helices A, B and C, respectively. GPI represents the glycophosphatidyl inositol anchor.

DETAILED DESCRIPTION OF PREFERRED EMBODIMENTS

Before the present peptides, small molecules, and assay methodology are described, it is to be understood that this invention is not limited to particular peptides, small molecules, assay methods, described and as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "PPMF" is used for Prion Protein Modulator Factor, which is a protein which can be glycosylated and is characterized by binding to $PrP^{C}$ and facilitating a conformational change from $PrP^{C}$ to $PrP^{Sc}$. The term encompasses any PPMF from any animal allowing for specific differences between different species of animals. The PPMF compounds of the present invention are more particularly characterized herein.

The term "pharmacophore" is used herein in an unconventional manner. Although the term conventional means a geometric and/or chemical description of a class or collection of compounds, as used here the term means a compound that has a specific biochemical activity which activity is obtained by the 3-dimensional physical shape of the compound and the electrochemical properties of the atoms making up the compound. Thus, as used here the term "pharmacophore" is a compound and not a description of a collection of compounds which have defined characteristics. Specifically, a "pharmacophore" is a compound with those characteristics. More specifically, pharmacophores of the invention may, for example, mimic or inhibit $PrP^{Sc}$ activity by interaction with (1) the discontinuous epitope on $PrP^C$ to which PPMF binds or (2) the surface of PPMF which binds to $PrP^C$. Thus, a pharmacophore of the invention has a shape (i.e., the geometric specifications) and electrochemical characteristics substantially as defined by $PrP^{Sc}$, PPMF, $PrP^C$, or other proteins involved in the prion complex that facilitate the conversion of $PrP^C$ to $PrP^{Sc}$. The term pharmacophore covers peptides, peptide analogs and small molecules.

The term "small molecule" as used herein refers to small organic compounds having a molecular weight of more than 50 and less than about 2,500 daltons, which preferably are not comprised of DNA or RNA.

The terms "treatment", "treating" and "treat" and the like are used herein to generally mean obtaining a desired pharmacological and/or physiological effect. The effect may be prophylactic in terms of completely or partially preventing a prion disease or symptom thereof and/or may be therapeutic in terms of partially or completely curing a prion disease or adverse effect attributable to the disease. The "treatment" as used herein covers any treatment of a disease in a mammal, particularly a cow, pig, sheep, mouse or human, and includes:

(a) preventing prion disease or symptoms from occurring in a subject which may be predisposed to the disease or symptom or infected with prion particles but has not yet been diagnosed as having a prion disease which can include the use of gene therapy;

(b) inhibiting prion disease symptoms, i.e., arresting the development of prion disease; or (c) relieving a prion disease symptom, i.e., causing regression of prion disease or prion disease symptoms.

The term "isolated" shall mean separated away from its natural environment. An isolated protein is not necessarily separated away from all materials it is normally present with and may remain glycosylated.

The term "corresponding position" means the position of an amino acid in a peptide or the position of a codon in a nucleotide sequence corresponding to the same position in the sequence of a different species. For example, the amino acid sequence of PPMF also has corresponding positions from one species to another and corresponding positions for four different positions on the discontinuous epitope of $PrP^C$ (for five different proteins) are shown in Table 1.

The term "FVB" refers to a mouse strain commonly used in the production of transgenic mice. For purposes of this invention it should be noted that the mouse prion protein (PrP) gene is intact and mouse PrP is therefore expressed at normal levels.

The term "$Prnp^{0/0}$" or "Prnp-Abl" refers to a transgenic animal which has its PrP gene ablated with the "$0/0$" indicating that both alleles are ablated whereas "$0/+$" indicates only one is ablated. Specifically, the animal being referred to is generally a transgenic mouse which has its PrP gene ablated i.e., a PrP knockout mouse. In that the PrP gene is disrupted no mouse PrP protein is expressed.

The term "sporadic CJD" abbreviated as "sCJD" refers to the most common manifestation of Creutzfeldt-Jakob Disease (CJD). This disease occurs spontaneously in individuals with a mean age of approximately 60 at a rate of 1 per million individuals across the earth.

The term "Iatrogenic CJD" abbreviated as "iCJD" refers to disease resulting from accidental infection of people with human prions. The most noted example of such is the accidental infection of children with human prions from contaminated preparations of human growth hormone.

The term "Familial CJD" refers to a form of CJD which occurs rarely in families and is inevitably caused by mutations of the human prion protein gene. The disease results from an autosomal dominant disorder. Family members who inherit the mutations succumb to CJD.

The term "Gerstmann-Strassler-Scheinker Disease" abbreviated as "GSS" refers to a form of inherited human prion disease. The disease occurs from an autosomal dominant disorder. Family members who inherit the mutant gene succumb to GSS.

The term "prion" shall mean an infectious particle known to cause diseases (spongiform encephalopathies) in humans and animals. The term "prion" is a contraction of the words "protein" and "infection" and the particles are comprised largely if not exclusively of $PrP^{Sc}$ molecules encoded by a PrP gene which expresses $PrP^C$ which changes conformation to become $PrP^{Sc}$. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

The terms "PrP gene" and "prion protein gene" are used interchangeably herein to describe genetic material which expresses PrP proteins, including proteins with polymorphisms and mutations such as those listed herein under the subheading "Pathogenic Mutations and Polymorphisms." Unless stated otherwise the term refers to the native wild-type gene and not to an artificially altered gene. The PrP gene can be from any animal including the "host" and "test" animals described herein and any and all polymorphisms and mutations thereof, it being recognized that the terms include other such PrP genes that are yet to be discovered. The term "PrP gene" refers generally to any gene of any species which encodes any form of a PrP amino acid sequences including any prion protein. Some commonly known PrP sequences are described in Gabriel et al., *Proc. Natl. Acad. Sci. USA* 89:9097–9101 (1992) and Wopfner et al., *J Mol Biol* 289:1163–78 (1999), which is incorporated herein by reference to disclose and describe such sequences.

The term "genetic material related to prions" is intended to cover any genetic material which affects the ability of an animal to become infected with prions. Thus, the term encompasses any "PPMF gene," "PrP gene," "artificial PrP gene," "chimeric PrP gene" or "ablated PrP gene" which terms are defined herein as well as mutations and modifications of such which affect the ability of an animal to become infected with prions. Standardized prion preparations are produced using animals which all have substantially the same genetic material related to prion so that all of the animals will become infected with the same type of prions and will exhibit signs of infection at about the same time.

The terms "host animal" and "host mammal" are used to describe animals which will have their genome genetically and artificially manipulated so as to include genetic material which is not naturally present within the animal. For example, host animals include mice, hamsters and rats which have their endogenous PrP gene altered by the insertion of an artificial gene or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions to which the test animal would generally be susceptible to infection. For example, the test animal may be a human, cow, sheep, pig, horse, cat, dog or chicken, and one may wish to determine whether a particular sample includes prions which would normally only infect the test animal. This is done by including PrP gene sequences of the test animal into the host animal, administering PPMF and inoculating the host animal with prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster. In general, prions of a given animal will not infect a genetically diverse animal and PPMF of a given animal will not bind to $PrP^C$ of a genetically diverse animal.

The terms "ablated prion protein gene," "disrupted PrP gene," "ablated PrP gene," "$PrP^{0/0}$" and the like are used interchangeably herein to mean an endogenous prion protein gene which has been altered (e.g., add and/or remove nucleotides) in a manner so as to render the gene inoperative. Examples of nonfunctional PrP genes and methods of making such are disclosed in Büeler, H., et al "Normal development of mice lacking the neuronal cell-surface PrP protein" Nature 356, 577–582 (1992) which is incorporated herein by reference. Both alleles of the genes are disrupted.

The terms "susceptible to infection" and "susceptible to infection by prions" and the like are used interchangeably herein to describe a transgenic or hybrid test animal which develops a prion disease if inoculated with prions which would normally only infect a genetically diverse test animal. The terms are used to describe a transgenic or hybrid animal such as a transgenic mouse Tg(MHu2M) which, without the chimeric PrP gene, would not be susceptible to infection with a human prion (less than 20% chance of infection) but with the chimeric gene is susceptible to infection with human prions (80% to 100% chance of infection).

The terms "resistant to infection", "resistant to infection with prions" and the like mean the animal includes a PrP gene which renders the animal resistant to prion disease when inoculated with an amount and type of prion which would be expected to cause prion disease in the animal. The resistant animals PrP gene includes non-native codons which express amino acids different from those of the native PrP gene which effect the $PrP^C$/PPMF binding site.

The term "incubation time" shall mean the time from inoculation of an animal with a prion until the time when the animal first develops detectable symptoms of disease resulting from the infection. A reduced incubation time is six months or less, preferable about 100 days±25 days or less, more preferably about 30 days±10 days or less.

ABBREVIATIONS USED HEREIN INCLUDE:

BSE for bovine spongiform encephalopathy;

CJD for Creutzfeldt-Jakob Disease;

CNS for central nervous system;

FFI for fatal familial insomnia;

GSS for Gerstmann-Strassler-Scheinker Disease;

Hu for human;

HuPPMF for human Prion Protein Modulator Factor;

HuPrP for a human PrP protein;

MHu2M for a chimeric mouse/human PrP gene wherein a region of the mouse PrP gene is replaced by a corresponding human sequence which differs from mouse PrP at 9 codons;

$MHu2MPrP^{Sc}$ for the scrapie isoform of the chimeric human/mouse PrP gene;

Mo for mouse;

MoPPMF for mouse Prion Protein Modulator Factor;

Mo PrP for a mouse PrP protein;

$MoPrP^{Sc}$ for the scrapie isoform of the mouse PrP protein;

PPMF for Prion Protein Modulator factor in general, i.e., that protein as in any species;

$Prnp^{0/0}$ for ablation of both alleles of an endogenous PrP protein gene, e.g., the Mo PrP gene;

$PrP^{CJD}$ for the CJD isoform of a PrP gene;

$PrP^{Sc}$ for the scrapie isoform of the PrP protein;

ScN2a for persistently infected scrapie mouse neuroblastoma cells also expressing $(MHM2)PrP^C$;

SHa for a Syrian hamster;

SHa PrP for a Syrian hamster PrP protein;

Tg for transgenic;

Tg(BovPrP) for transgenic mice containing the complete cow PrP gene;

Tg(HuPrP) for transgenic mice containing the complete human PrP gene;

$Tg(HuPrP)/Prnp^{0/0}$ for a hybrid mouse obtained by crossing a mouse with a human PrP protein gene (HuPrP) with a mouse with both alleles of the endogenous PrP protein gene disrupted;

Tg(MHu2M) mice are transgenic mice of the invention which include the chimeric MHu2M gene;

$Tg(MHu2M)/Prnp^{0/0}$ for a hybrid mouse obtained by crossing a mouse with a chimeric PrP protein gene (MHu2M) with a mouse with both alleles of the endogenous PrP protein gene disrupted;

Tg(SHa PrP) for a transgenic mouse containing the PrP gene of a Syrian hamster;

$Tg(SHa\ PrP^{+/0})81/Prn\text{-}p^{+/0}$ for a particular line (81) of transgenic mice expressing. SHa PrP, +/0 indicates heterozygous; and Tg(SHa PrP) for transgenic mice containing the complete sheep PrP gene.

GENERAL ASPECTS OF THE INVENTION

The present invention is based on the discovery that synthetic or isolated molecules (e.g. small molecules, peptides, and the like) with the appropriate tertiary structure have the ability to interact with members of the prion replication complex and to inhibit the formation of de novo protease resistant forms of PrP in appropriate animals.

PHARMACOPHORE DESIGN AND THE $PrP^C$-PPMF INTERFACE $PrP^C$ forms a complex with PPMF and $PrP^{Sc}$ resulting in a ternary complex of PPMF/$PrP^C$/$PrP^{Sc}$. After the conversion of PrP$^C$ to PrP$^{Sc}$, the complex dissociates due to the lack of affinity of PrP$^{Sc}$ for PPMF. To inhibit this PrP$^{Sc}$ replication cycle, pharmacophores fitting this geometric and chemical description are used to interfere with either the PrP$^{Sc}$/PrP$^C$ or PPMF/PrP$^C$ interface. The inhibitors can be used to prevent the initial conversion of PrP$^C$ into prions, or later prevent the progression of prion formation.

The PrP$^{Sc}$ binding site on the surface of the PrP(90–231) NMR structure appears to form a rather large and discontinuous epitope (Scott, et al., 1997). Accordingly, we have focused on pharmacophores that preferably mimic the PPMF binding site on the surface of PrP$^C$. Identifying pharmacophores of the invention requires the identification of small molecules, peptides, and the like that mimics the positive image of the residues that comprise the PPMF binding site on the surface of the PrP(90–231) NMR structure. A successful compound binds to PPMF, modifying its action, and thereby inhibiting prion replication.

CONVERSION THEORY

In general, deposition diseases such as the prion diseases appear to follow the form:

$$A \leftrightharpoons A^* \leftrightharpoons B \rightarrow B_n$$

where A is the normally synthesized gene product that carries out an intended physiologic role in a monomeric or oligomeric state, A* is an conformationally activated form of A that is competent to undergo a dramatic conformational change, B is the conformationally altered state that prefers multimeric assemblies and $B_n$ is the multimeric material that is pathogenic and relatively difficult to recycle. For the prion diseases, PrP$^C$ and PrP$^{Sc}$ correspond to states A and $B_n$ where A is largely helical and monomeric and $B_n$ is β-rich and multimeric.

Two types of kinetic barriers can be imagined that restrict the formation of $B_n$. If the protein in question is relatively large and the conformations of A and B are quite different, then a largely enthalpic kinetic barrier could exist where B can act as a template to reduce the barrier to the conformational change. Alternatively, if a smaller peptide is undergoing the dramatic conformational reorganization (as with βAPP in Alzheimer's disease (Jarrett & Lansbury, Ann N Y Acad Sci. 695:144–8 (1993) or calcitonin in medullary carcinoma of the thyroid or a smaller conformation change is sufficient (as in sickle cell hemoglobin fibril formation (Mirchev & Ferrone, J Mol Biol. 265:475–9 (1997)) the rate limiting step may be the formation of a stable multimeric nucleus ($B_n$).

Figure 4:
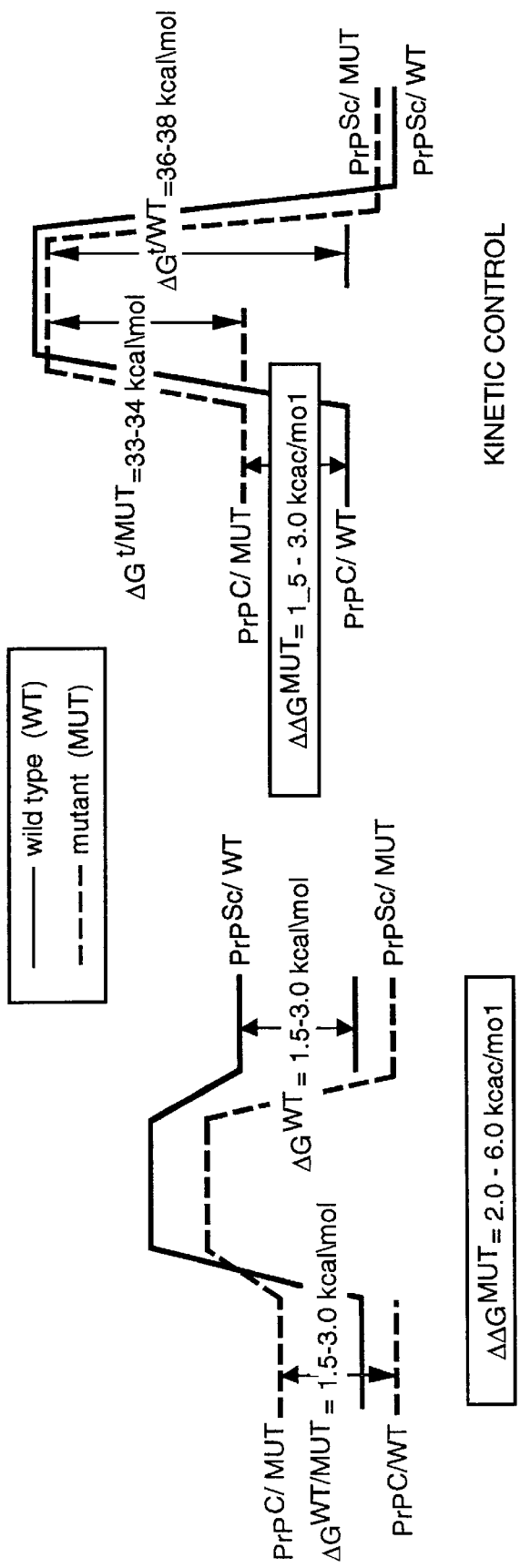
Figure 5:
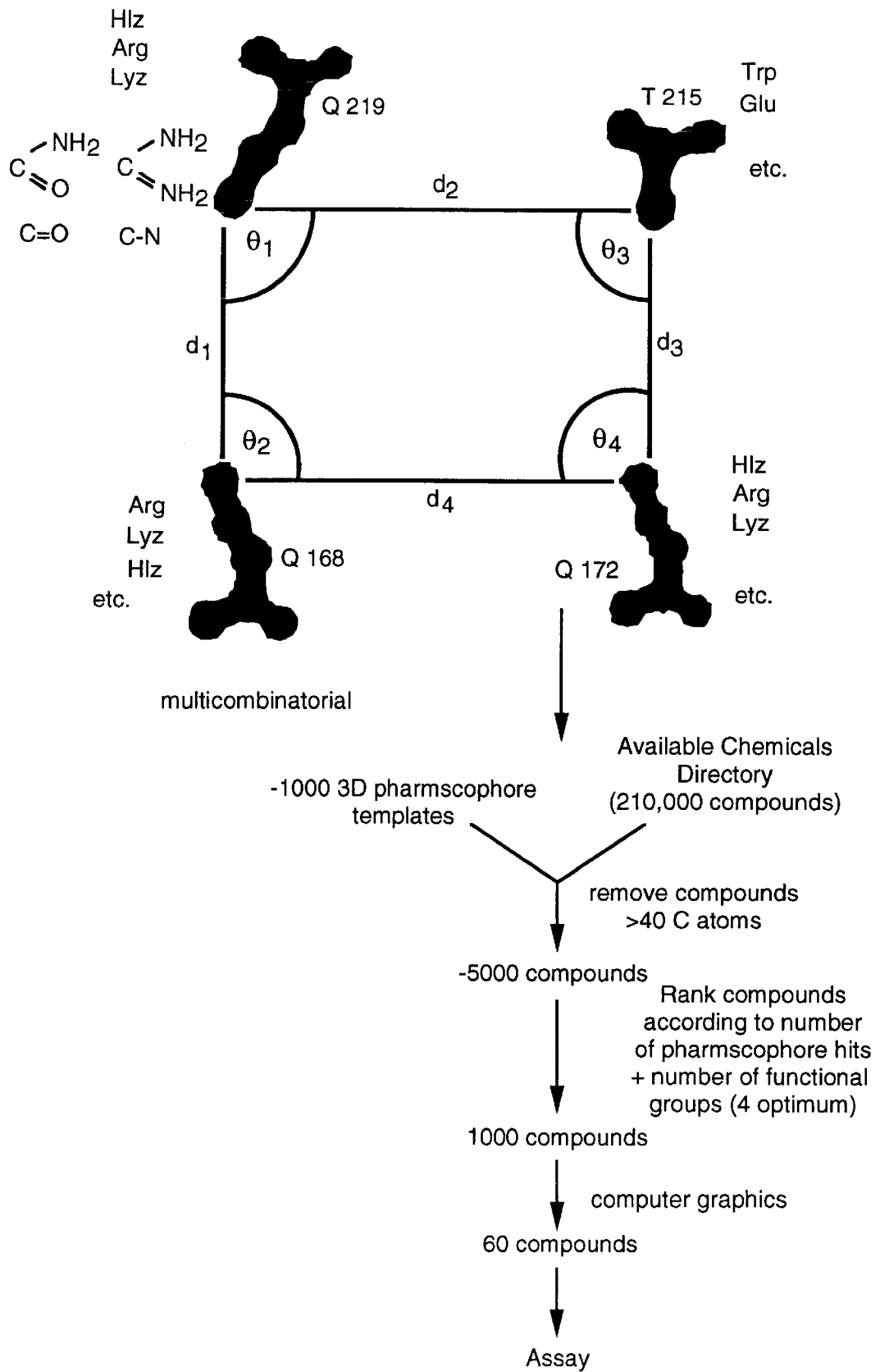
Figure 6:
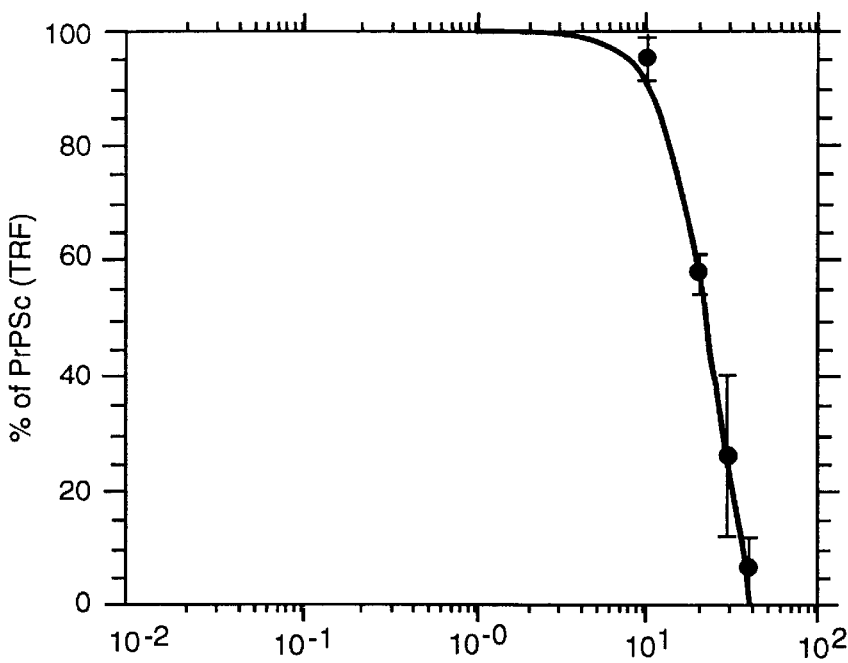

Without being bound to any particular theory, PrP$^{Sc}$ formation is believed to require an escape from the kinetically trapped monomeric PrP$^C$ structure. See FIG. 4. For example, PrP$^{Sc}$ formation is a first order process where the time from inoculation to disease doubles when the gene dose is changed in animals homozygous and hemizygous for the prion gene. In transgenic animals carrying a mutant gene that causes a spontaneous prion disease, the time to disease is halved when the founder animals are crossed to yield a progeny carrying twice the transgene dose (Cohen & Prusiner, Annu Rev Biochem. 67:793–819 (1998)). The conformational transformation of a monomeric chain follows first order kinetics, while the rate equation for nucleation events follows higher order kinetics dictated by the multimeric state of the nucleus.

The concept of PrP$^{Sc}$ providing a template to assist the conversion of nascent PrP$^C$ molecules implies that some PrP$^{Sc}$ templates should be more efficient at stabilizing the nascent PrP$^{Sc}$ molecule than others in the initial phase of disease propagation. This can be seen in the species barrier to prion transmission where SHa PrP$^{Sc}$ is less efficient than MoPrP$^{Sc}$ in causing disease in mice, and HuPrP$^{Sc}$ is even less efficient than SHa PrP$^{Sc}$(Scott, et al., Cell 73:979–88 (1993); Telling, et al., Proc Natl Acad Sci US. 91:9936–40 (1994); Scott, et al., Proc Natl Acad Sci USA, 94:14279–84 (1997). For humans, HuPrP$^{Sc}$ provides the most effective inoculum, but it has become clear the BoPrP$^{Sc}$ can cause disease in humans albeit at a much lower frequency (Hill, et al., 1993). There is no evidence that SHaPrP$^{Sc}$ has ever caused disease in humans. It follows that one portion of the molecule is involved in the PrP$^{Sc}$ species specific features of the inoculum while a distinct surface of the molecule is available for interaction with a distinct species specific PPMF molecule. Dominant negative mutations to the PrP gene have been identified that prevent wild type PrP$^{Sc}$ replication apparently by sequestering PPMF (Telling, et al., Cell 83:79–90 (1995); Kaneko, et al., Proc Natl Acad Sci USA 94:10069–74 (1997)). Epidemiologic studies have suggested the existence of dominant negative mutations in humans and sheep that act via this mechanism (Prusiner, et al., Proc Natl Acad Sci USA 95:13363–83 (1998)).

The target size of the infectious particle is 55 kDa, a feature corresponding to a dimer (Bellinger-Kawahara, et al., Virology 164:537–41 (1988)). Identification has been made of four residues that are important to the human PrP$^C$-PPMF interaction: 168, 172, 215 and 219. In the NMR structures of various recombinant forms of PrP$^C$, residues 172, 215 & 219 form a continuous patch on the molecular surface. Residues 170 & 171 are a part of this surface, but mutagenesis experiments demonstrate that they do not participate in this interaction while 168 is clearly not part of this surface in the known structure. However, if the α-helix is extended by one turn toward the N-terminus to include residue 168, a continuous surface is formed (James, et al., Proc Natl Acad Sci USA 9410086–91 (1997). Wallace, et al., PNAS (1999) have suggested that this reorganization of the molecule creates an A* state that is conversion competent.

Pharmacophores of the present invention take advantage of this conversion process, and preferably have structural aspects that prevent the conversion of PrP$^C$ to its conversion competent state (e.g inhibitory pharmacophores). In one example, by binding to PrP$^C$ or to a protein that interacts with PrP (e.g. PPMF at its PrP$^C$ binding domain) a pharmacophore of the present invention may block PrPC:protein interactions and prevent the conversion process.

PrP POLYMORPHISMS AND MUTATIONS

The PrP pharmacophores of the present invention optionally contain one or more polymorphisms or mutations known to facilitate prion formation. There are a number of mutations and polymorphisms existing with respect to the PrP gene of different species. A number of the mutations and polymorphisms are listed in the "Mutation Table" provided below. It is believed that additional mutations and polymorphisms exist in all species within the PrP gene. Substitutions in the refraction inhibitor pharmacophore may be made with an amino acid which is biochemically quite different from the amino acid at that position which is known to render the animal susceptible to prion infection. Thus, if a basic and/or polar amino acid is present at the critical site that site could be replaced with an acidic and/or nonpolar amino acid. With these criteria in mind some trial and error would be required. Acidic amino acids should be substituted with basic amino acids and vice versa. Polar amino acids should be substituted with nonpolar amino acids and vice versa. Such mutations may increase efficacy of the pharmacophores for the uses described herein.

There are a number of known pathogenic mutations in the human PrP gene. Further, there are known polymorphisms in the human, sheep and bovine PrP genes. The following is a list of such mutations and polymorphisms:

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Gln | |
| 4 octarepeat insert | Codon 219 Glu/Lys | Codon 136 Ala/Val | |
| 5 octarepeat insert | | Codon 154 Arg/His | 5 octarepeat insert |
| 6 octarepeat insert | | | 6 octarepeat insert |
| 7 octarepeat insert | | | 7 octarepeat insert |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al., *Proc. Natl. Acad. Sci. USA* 89:9097–9101 (1992). The sequence for the Syrian hamster is published in Basler et al., *Cell* 46:417–428 (1986). The PrP gene of sheep is published by Goldmann et al., *Proc. Natl. Acad. Sci. USA* 87:2476–2480 (1990). The PrP gene sequence for bovine is published in Goldmann et al., *J. Gen. Virol.* 72:201–204 (1991). The sequence for chicken PrP gene is published in Harris et al., *Proc. Natl. Acad. Sci. USA* 88:7664–7668 (1991). The PrP gene sequence for mink is published in Kretzschmar et al., *J. Gen. Virol.* 73:2757–2761 (1992). The human PrP gene sequence is published in Kretzschmar et al., *DNA* 5:315–324 (1986). The PrP gene sequence for mouse is published in Locht et al., *Proc. Natl. Acad. Sci. USA* 83:6372–6376 (1986). The PrP gene sequence for sheep is published in Westaway et al., *Genes Dev.* 8:959–969 (1994). These publications are all incorporated herein by reference to disclose and describe the PrP gene and PrP amino acid sequences.

LOCALIZATION OF PHARMACOPHORES WHICH INHIBIT PrP$^{Sc}$ REPLICATION

PrP$^{Sc}$ formation is likely to take place in the caveolar space. Thus, the inhibitors that follow the pharmacophores of the present invention may be lipidated to increase their efficacy. Pharmacophore inhibitors can be membrane associated by attachment of a covalent linkage to a fatty acid. Prenylation, farnesylation, geranylgeranylation, palmitoylation and myristilation are exemplary modifications that would increase localization of the inhibitor of the invention to the membrane. Linkage to molecules such as cholesterol can also be used to affect localization of the protein.

ASSAYS TO IDENTIFY INHIBITOR PHARMACOPHORES

Candidate molecules as inhibitory pharmacophores can encompass numerous chemical classes, including, but not limited to, peptides and small molecules. Candidate pharmacophores can comprise finctional groups necessary for structural interaction with proteins, particularly hydrogen bonding, and typically include at least an amine, carbonyl, hydroxyl or carboxyl group, preferably at least two of the functional chemical groups. The candidate pharmacophores often comprise cyclical carbon or heterocyclic structures and/or aromatic or polyaromatic structures substituted with one or more of the above functional groups. Candidate inhibitor pharmacophores are also found among biomolecules including, but not limited to: polynucleotides, peptides, saccharides, fatty acids, steroids, purines, pyrimidines, derivatives, structural analogs or combinations thereof.

Candidate inhibitor pharmacophores can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacologically relevant scaffolds may be subjected to directed or random chemical modifications, such as acylation, alkylation, esterification, amidification, etc. to produce structural analogs.

Inhibitors that modulate molecules involved in prion complex formation and/or PrP$^{Sc}$ conversion can be identified using binding sites on molecules involved in the prion complex, e.g. PrP and PPMF. For example, residues 168, 172, 215 and 219 on the surface of the human PrP$^{C}$ molecule are known to contribute to the integrity of the PrP$^{C}$-PPMF interface, and thus these molecules define finctional residues on a binding site of PrP. Identification of structural aspects of proteins involved in prion complex formation, such as the side chains involved in the PPMF/PrP$^{C}$ interaction, can define a tertiary structure to be used in an assay to design pharmacophores that modulate molecules and/or protein-:protein interactions in the prion complex. Specifically, a dataset of compounds (small molecules, peptides, etc) having a particular tertiary structure can be identified using techniques known in the art, such as medicinal chemistry, combinatorial chemistry and molecular modeling, to determine molecules that are likely to bind to the atoms or groups of atoms of a protein involved in prion complex formation and/or conversion of PrP$^C$ to PrP$^{Sc}$. Optionally, factors such as hydrophobicity and hydrophilicity, placement of the functional residues in a structural motif, and mutations involved in prion mediated disorders may also be taken into account.

Figure 7:
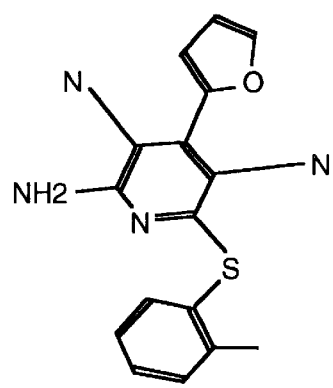

In a preferred embodiment of the assay of the invention, the assay involves (1) matching compounds in a library with the binding site regarding spatial orientation; (2) screening candidate compounds visually using computer generated molecular display software; and (3) experimentally screening actual compounds against PrP$^C$ in the presence of PrP$^{Sc}$ to determine compounds which inhibit or enhance conversion of PrP$^C$ to PrP$^{Sc}$. This methods is shown schematically in FIG. 7.

Once the functional residues of the target protein (e.g. PPMF) are identified, this portion of the molecule can serves as a template for comparison with known molecules, e.g., in a database such as Available Chemicals Database (ACD, Molecular Design Labs, 1997), or it may be used to design molecules de novo. In one example, the initial group of identified molecules may contain tens or hundreds of thousands or more of different non-peptide organic compounds. A different or supplemental group may contain millions of different peptides which could be produced synthetically in chemical reactions or via bacteria or phage. Large peptide libraries and methods of making such are disclosed in U.S. Pat. No. 5,266,684, issued Nov. 30, 1993, and U.S. Pat. No. 5,420,246, issued May 30, 1995, which are incorporated herein by reference. Libraries of non-peptide organic molecules are disclosed in PCT publication WO 96/40202, published Dec. 19, 1996, incorporated herein by reference.

The initial library of molecules is screened via computer generated modeling, e.g., computer models of the compounds are matched against a computer model of the PPMF binding site on $PrP^C$ to find molecules which mimic the spatial orientation and basic polymorphism of PPMF. This screening should substantially reduce the number of candidate molecules relative to the initial group.

The screened group is then subjected to further screening visually using a suitable computer program which makes viewable images of the molecules. The resulting candidate molecules are then actually tested for their ability to inhibit $PrP^{Sc}$ formation.

Screening of Candidate Pharmacophores In Vivo

A collection of small molecules or peptides can be screened for their ability to affect prion conversion or to mitigate an undesirable phenotype (e.g., a symptom) associated with prion-mediated disease, e.g. neuropathy. The candidate pharmacophores can be screened in either non-transgenic animals or in animals that are transgenic for an alteration in $PrP^C$, and preferably in a transgenic animal with an ablated, endogenous PrP gene, and even more preferably a transgenic animal with an ablated, endogenous PrP gene and an expressed, exogenous PrP gene from a genetically diverse animal that is the target of the pharmacophore, e.g. a $PrP^{0/0}$Tg(MHuM).

In general, the candidate pharmacophore is initially tested in an ex vivo cellular array of prion replication optimized using the tools of medicinal chemistry and then administered to a non-human, transgenic animal, and the effects of the candidate determined. The candidate pharmacophore can be administered in any manner desired and/or appropriate for delivery of the small molecules or peptides in order to effect a desired result. For example, the candidate pharmacophore can be administered by injection (e.g., by injection intravenously, intramuscularly, subcutaneously, or directly into the tissue in which the desired affect is to be achieved), orally, or by any other desirable means, and preferably is administered intercerebrally. Normally, the in vivo screen will involve a number of animals receiving varying amounts and concentrations of the candidate therapeutic (from no therapeutic candidate to an amount of the candidate that approaches an upper limit of the amount that can be delivered successfully to the animal), and may include delivery of the pharmacophore in a different formulation. The pharmacophore can be administered singly or can be combined in combinations of two or more, especially where administration of a combination of pharmacophores may result in a synergistic effect.

To speed development the pharmacophore is tested initially in a cellular system such as ScN2a cells or the cellular system disclosed in U.S. Ser. No. 09/318,888, which is incorporated herein by reference.

PHARMACEUTICAL COMPOSITIONS

The present invention also encompasses pharmaceutical compositions comprising small molecules or peptides fitting the chemical and geometric constraints of the pharmacophores for reducing, inhibiting, or otherwise mitigating plaque formation or prion replication in a subject susceptible to neuronal degenerative disorders associated with protein deposit formation.

Formulations

Pharmaceutical formulations of the invention preferably contain small molecules or peptides of the present invention. They may also be used in appropriate association with other pharmaceutically active compounds. The following methods and excipients are merely exemplary and are in no way limiting.

For oral preparations, the small molecules or peptides fitting the chemical and geometric constraints of the pharmacophores can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol. The formulations may also contain conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

For use in the subject methods, the compounds may be formulated with other pharmaceutically active agents, particularly other agents that can modulate onset or symptoms of the condition to be treated. For example, to treat Alzheimer's disease or CAA, the polycation compound can be co-administered with one or more biologically active agents that reduce protein deposit formation and/or prevent protein deposit formation. Examples of such compounds include nonsteroid anti-inflammatory drugs (NSAIDs) or aspirin-like drugs (J. R. Vane, *Semin Arthritis Rheum* 26:2–10 (1997)), selective inhibitors of COX-2 (J. R. Vane *Int J Tissue React*, 20:3–15 (1998)), protein phosphatases that act on microtubule-associated protein tau protein phosphatases (K. Iqbal, *Ann N Y Acad Sci* 777:132–8 (1996)), modulators of APP proteolytic enzymes and apoE activity (P. T. Lansbury Jr, *Arzneimittelforschung* 45:432–4 (1995)), inhibitors of polysaccharides, such as glycosaminoglycan and proteoglycans, (B. Leveugle et al., *Neuroreport* 5:1389–92 (1994)) and the like. The additional active ingredients may be conjugated to the pharmacophore or may be contained separately within a formulation.

The formulations of the invention have the advantage that they are non-toxic in tested forms of administration. For example, parenteral administration of a solution of the formulations of the invention is preferably nontoxic at a dosage of 0.1 mg/mouse, which is an $LD_{50}$ of less than one at 40 mg/Kg.

Administration

Administration of a compound of the invention may be accomplished by any convenient means, including parenteral injection, and direct intracerebral injection or continuous (e.g., long-term or chronic) infusion. The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intratracheal, etc., administration. The active agent may be systemic after administration or may be localized by the use of regional administration, intramural administration, or use of an implant that acts to retain the active dose at the site of implantation.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing sensitizer is placed in proximity to the site of protein deposits (e.g., the site of formation of amyloid deposits associated with neurodegenerative disorders), so that the local concentration of active agent is increased at that site relative to the rest of the body.

The formulations can also be administered by infusion into the brain, and may be administered in either a continuous (e.g., sustained) or non-continuous fashion. Methods, formulations, and devices suitable for delivery to the brain in a continuous (e.g., chronic) or non-continuous (e.g., single, discrete dose per administration) fashion are described in, for example, U.S. Pat. Nos. 5,711,316; 5,832,932; 5,814,014; 5,782,798; 5,752,515; 5,735,814; 5,713,923; 5,686,416; 5,624,898; 5,624,894; 5,124,146; and 4,866,042 (delivery of genetic material).

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The compound for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosage

Depending on the patient and condition being treated and on the administration route, the compounds of the invention will generally be administered in dosages of 0.001 mg to 5 mg/kg body weight per day. The range is broad, since in general the efficacy of a therapeutic effect for different mammals varies widely with doses typically being 20, 30 or even 40 times smaller (per unit body weight) in man than in animal models (e.g., in the transgenic mice described herein). Similarly the mode of administration can have a large effect on dosage. Thus for example oral dosages in the mouse may be ten times the injection dose. Still higher doses may be used for localized routes of delivery.

A typical dosage may be: a solution suitable for intravenous administration; a tablet taken from two to six times daily; or a one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Binding Site in PrP$^C$ for PPMF

An examination of the amino acids which distinguish Hu PrP from Mo PrP shows only seven residues at the C-terminus (168–231) that are different. Four ofthese residues are close to the glycophosphatidylinosytol (GPI) anchor attached to Ser231 while the remaining three residues were within or near the C-terminus of a postulated -helix which has been conformed by NMR structural studies. To identify the critical binding site within PrP$^C$ for PPMF the seven residues were divided into two groups: those at the C-terminal end of the last -helix (HuA) and those at the extreme C-terminus (Hub). The Mo residues were replaced with Hu counterparts in positions that were critical for binding of PrP$^C$ to Mo PPMF to determine the effect of such on inhibiting the formation of recombinant PrP$^{Sc}$. Recombinant PrP$^{Sc}$ was distinguished from endogenous wild-type (wt) Mo PrP$^{Sc}$ by using the SHa/Mo chimeric PrP designated MHM2 that contains a binding site for the anti-SHa PrP 3F4 monoclonal antibody (mAb).

Three chimeric constructs, denoted as MHMHUA (Mo residues 214, 218 and 219 were replaced with the corresponding human residue), MHMHuB (Mo residues 226 through 230 replaced with Hu), and MHMHu(A+B) (combined replacements), were transiently transfected into scrapie infected Mo neuroblastoma (ScN2a) cells. Neither MHMHu(A+B) nor MHMHuA was converted into PrP$^{Sc}$ as judged by the acquisition of protease resistance. By contrast, MHMHuB was converted into PrP$^{Sc}$ as efficiently as the control MHM2. These results indicate that Mo PPMF did not bind to MHMHu(A+B) or to MHMuA but did bind to MHMHuB and MHM2, both of which were converted into Prp$^{Sc}$.

Example 2

Identification of Inhibitory Pharmacophores

Alanine scanning mutagenesis (Wells, 1991, *Methods Enzymol.* 202:390–411) has been used to estimate experimentally the binding contribution of single residues to a protein-protein interaction. For prion replication, residues 168, 172, 215 and 219 on the surface of the human PrP$^C$ molecule contribute the most to the integrity of the PrP-PPMF interface. Indeed, substitution for basic residues at this site increases the affinity of PrP for PPMF sufficiently to block the replication cycle. Thus, those side chain sites define a plausible 3D pharmacophore target for mimetic design. In particular, the sidechain coordinates of residues Q168, Q172, T215 and Q219 from the PrP(90-231) NMR structure as well as the coordinates of residue Q168 when helix B is extended to residue 166.

Since basic residues at Q168, Q172 and Q219 and acidic or hydrophobic residues at T215 increase the affinity of PPMF for PrPC, Arg, Lys, His, Asp, Glu and Trp were modeled onto the relevant residue positions of the PrP(90-231) NMR structure using the program SCWRL Using these coordinates, a dataset of 3D pharmacophores were created in a combinatorial fashion using all the atoms comprising a sidechain as well as only the functional atoms. The fact that residue Q168 may be part of helix B rather than occupy the position suggested by the PrP(90-231) NMR structure was also taken into account.

Mutational data suggests that substitution of more than one basic residue at the PPMF site led to PrP molecules that could not inhibit scrapie formation in a dominant negative fashion. With this mind, the relevant 3D pharmacophores that had more than one basic residue were filtered from the 3D pharmacophore dataset as necessary. This resulted in ~1000 templates that were compared with the 210,000 compounds present in the Available Chemicals Database (ACD, Molecular Design Labs, 1997) for compounds that mimic both the spatial orientation and basic polymorphism present in the dataset of 3D pharmacophores.

To speed up the search through the compound database, the graph theory algorithm of Ullman was employed. This approach has been utilized to aid comparison of protein structures and to search for ligands and sidechain patterns in the Protein Data bank (PDB). Our algorithm has two main stages. Firstly, the covalent connectivity of the pharmacophore sidechains are compared to the compounds. If at least one match for each of these sidechains is located within the compound, then the distances and angles between these substructures are then compared to the pharmacophore. This approach confers considerable flexibility to the program and facilitates the search for substructures within a 3D pharmacophore that are connected both covalently and non-covalently. 45 minutes of CPU time were required to perform a single search with a 3D pharmacophore so ~15 days were required using a Silicon Graphics Indigo 2 workstation to search with ~1000 3D pharmacophores templates against the ACD. Compounds were scored according to the number of 3D pharmacophore elements that they matched as well as the number of functional groups that they present (where 4 is the optimal solution which is equal to the number of residues present on the PPMF binding site on PrP$^C$).

Following visual screening of the ~1000 compounds for a variety of structural medicinal and toxicologic concerns, a total of 63 compounds were selected for screening. The effect of the 63 compounds tested on transiently transfected ScN2a cells is summarized below in Table 1.

| Number | Compound Name | Results |
|---|---|---|
| Nucleic Acid derivatives | | |
| 3 | α-Adenosine | Negative |
| 7 | 1, N6-Ethenoadenosine-5'-Monophosphate | Positive |
| 10 | Cytidylyl (3'5') Guanosine | Negative |
| 17 | 2'3'-Di-O-Acetylguanoside | Negative |
| 18 | Purine Riboside | Positive |
| 26 | Hydroxyguanidino-purine Riboside | Negative |
| 27 | Adenylyl (3'5')Cytidine | Negative |
| 28 | Guanylyl (2'5')Guanosine | Negative |
| 32 | 2'3'-Di-O-Acetyladenosine | Positive |
| 29 | Adenosine 2'3'cyclic monophosphase sodium salt | Negative |
| 33 | Guanosine 2'3' | Negative |
| 35 | Adenosine 5'-Carboxylic Acid | Negative |
| 36 | Inosine 3'-Monophosphate | Negative |
| 40 | 2'-O-Anthramiloy Indenosine 3'5'-Cyclic Monophosphate | Negative |
| 51 | 2,5 Dimethoxy-phenylguanidine Carbonate | Negative |
| Amino acid and peptide derivatives | | |
| 2 | Naphtha (Terbutoxycarbonyl)-L- | Negative |

-continued

| Number | Compound Name | Results |
|---|---|---|
|  | Arginine |  |
| 6 | Chloroacetyl-DL-Nortencine | Negative |
| 34 | MTH-DL-Arginine HCI | Negative |
| 45 | N Phrhaloyl-DL-Histidine | Negative |
| 48 | n-alphabenzoyl-L-Histidinol | Negative |
| 5 | H-Ala-Arg-Oh Acetate | Negative |
| 20 | PGlu-Gly-Arg-Phe Amide | Negative |
| 30 | [Mei(O)4, D-Lyss, Pho9]-Fragment 4-9 | Negative |
| 49 | BOC-Val-Gly-Arg-βNa-AcOH | Negative |
| 54 | Z-ARG-OBZL (P-NO2)HBR | Negative |
| 55 | [Glu]-TRH | negative |
| 57 | Leu-Asp-Val-Pro-Ser | Negative |
|  | Antibiotics |  |
| 9 | Neamine | Negative |
| 15 | Butirosin Disulfate Salt | Negative |
| 16 | Puromycin Aminonucleoside | Negative |
| 19 | Geneticin | Negative |
| 21 | Ribostamycin | Negative |
| 22 | Dibekacin | Negative |
| 23 | Sisomycin | Negative |
| 39 | Amikacin | Negative |
| 41 | Trimellitic Acid Amide | Negative |
| 42 | Streptomycin | Negative |
|  | Diverse compounds |  |
| 1 | Urocanic Acid | Negative |
| 13 | Caffeine | Negative |
| 14 | 4',6-Diamidino-2 Phenylindole | Negative |
| 25 | Amidinophenyl (6 Amidino-2-indolyl)Phenyl Ether | Negative |
| 37 | Amino Imidazole Carobxamidoxime | Negative |
| 38 | Allentoic Acid | Negative |
| 44 | 1,1, Thhiobis 5,5' Dimethyl hydratoin | Negative |
| 46 | 7-acotoxy mthyl 6 benzamido hexah 7 methyl 5 oxoimidazo | Negative |
| 47 | 3 mitro 4,4' methylamediamiline | Negative |
| 53 | Z-Phenyl-Arginyl-7-Amido-4-Methylcoumarin Hcl | Negative |
| 64 | Isoxazol diazaspito | Negative |
| 65 | 4 Nitro Phenyl Methoxy Benzoyl | Negative |
| 66 | 6-Morpholino-5-Nitroimidazol | Negative |
| 56 | KM-04966 | Negative |
| 59 | RJF-00556 | Negative |
| 60 | KM-00561 | Positive |
| 61 | NRB-04485 | Negative |
| 62 | KM-06274 | Positive |
| 69 | Amiloride-HCI | Negative |
| 70 | KM-06272 | Negative |
| 71 | KM-06273 | Negative |
| 72 | KM-06278 | Negative |
| 73 | KM-06280 | Negative |
| 74 | KM-06281 | Negative |
| 75 | CD-05250 | Negative |
| 76 | SEW-105 | Negative |

Transiently transfected ScN2a cells were incubated with 10 uM KM-00561 for 3 days. Protein-immunoblotting analysis of the lysates were performed before (PK−) and after (PK+) proteinase K gestion. For immunoblotting, the monoclonal antibody mAb3F4 was used. Compounds were purchased from the appropriate supplier, dissolved in 5% DMSO and incubated with scrapie infected neuroblastoma cells at a variety of concentrations. Administration of 5% DMSO with no compound was used as a negative control, and mevastatin in 5% DMSO was used as a positive control. Experiments showing compounds that present an inhibitory effect on $PrP^{Sc}$ formation in ScN2a cells have been repeated at least 3 times.

Figure 8:
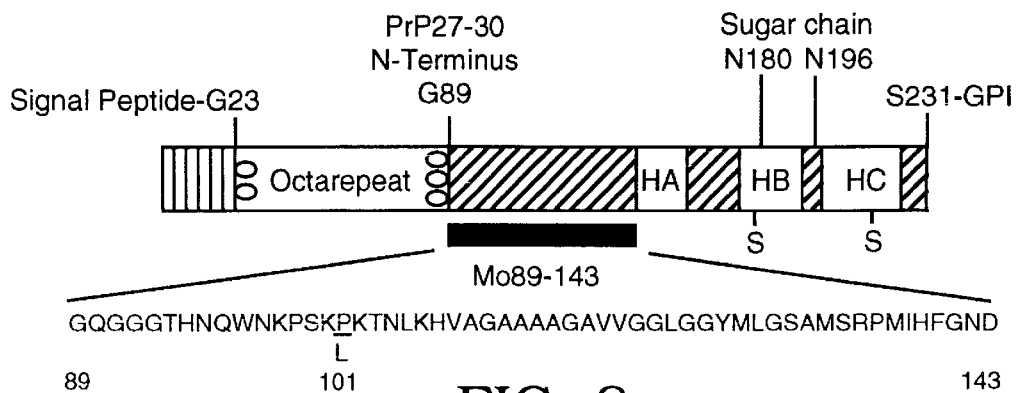

The production of proteinase K resistant $PrP^{Sc}$ can be followed as a finction of concentration of the various compounds. Compounds 18, 32, 62 and 60 were effective at inhibiting $PrP^{Sc}$ formation at 20–40 $\mu$M concentrations. FIG. 8 illustrates a dose response curve looking at the effect of compound 60 on $PrP^{Sc}$ production using the quantitative assay of Safar, et al., (1998) which shows an $IC_{50}$=20 $\mu$M. While nanomolar potency is normally sought in enzyme and receptor based screening assays, our results are close to the single digit micromolar concentrations frequently accepted as "hits" in complex cell based screening assays (e.g., antimicrobial agents).

Figure 9:
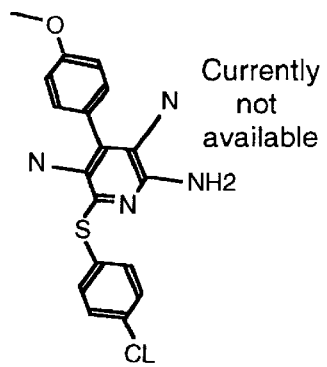
Figure 9:
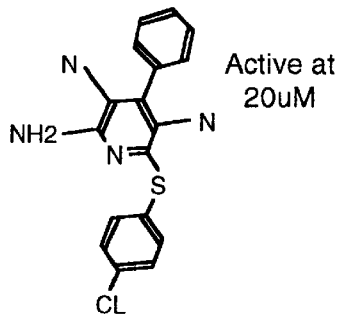
Figure 9:
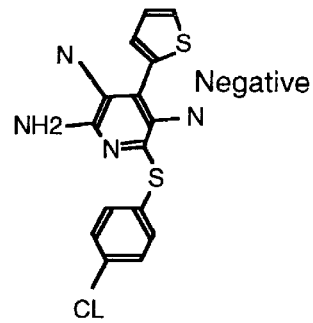
Figure 9:
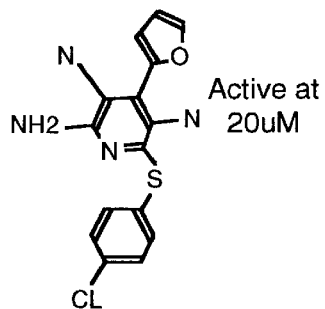
Figure 9:
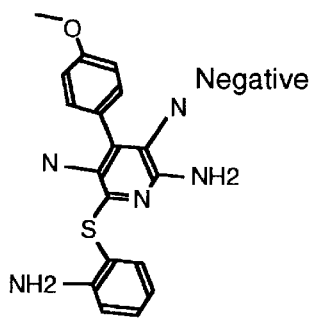
Figure 9:
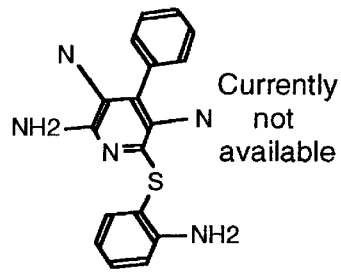
Figure 9:
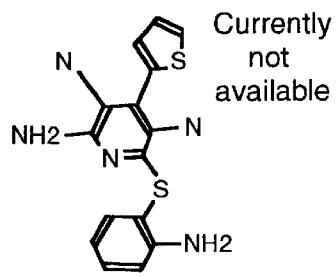
Figure 9:
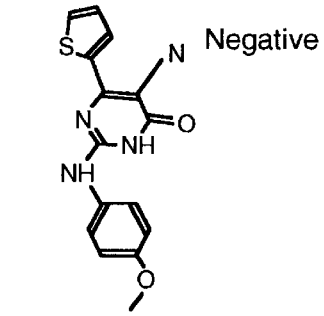
Figure 9:
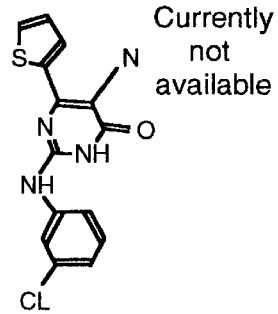

A limited structure/activity relationship was obtained by screening a series of nine similar compounds. FIG. 9 shows compound 60 (the original lead compound) and the preliminary screening data at a single concentration for six of the related compounds that are commercially available. Substituted pyridines are a relatively easy target for analog development. The quantitative assay results can be used to determine $IC_{50}$'s for each of the analogs in FIG. 10 and then to develop a synthetic plan for building a structure activity relationship.

Example 3

Targeting the Inoculum to the Caveolar Space of Neuronal Cells

From a variety of studies, it has become clear that $PrP^{Sc}$ formation is likely to take place in the caveolar space. However, there is no specific reason why the refolded β-rich peptides should preferentially concentrate in this region. PrP targeted to clatharin coated pits is not converted into $PrP^{Sc}$. Since PrP is GPI anchored, lipidating the C-terminus of a polypeptide pharmacophore should improve cell localization. Accordingly, the Mo 89-143, P101L peptide was myristylated and applied to cells. The lipidated peptide can then localize to the cell surface and be internalized into endocytic vesicles.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An assay to identify a PrP pharmacophore, said assay comprising the steps of:

determining functional residues of the PrP protein involved in prion complex interactions;

developing a plurality of three dimensional structures based on these functional residues;

comparing the plurality of three dimensional structures with a series of compounds having calculatable tertiary structures; and identifying compounds having a spatial orientation consistent with binding PrP at the determined functional residues.

* * * * *